(12) United States Patent
Zhang

(10) Patent No.: US 10,307,241 B2
(45) Date of Patent: Jun. 4, 2019

(54) EMBOLIC PROTECTION DEVICES AND METHODS OF USE

(71) Applicant: CardioVantage Medical, Inc., San Mateo, CA (US)

(72) Inventor: Ji Zhang, Burnaby (CA)

(73) Assignee: Suzhou Jiecheng Medical Technology Co., Ltd., WuJiang, Jiangsu (CN)

( * ) Notice: Subject to any disclaimer, the term of this patent is extended or adjusted under 35 U.S.C. 154(b) by 305 days.

(21) Appl. No.: 14/774,053

(22) PCT Filed: Mar. 11, 2014

(86) PCT No.: PCT/US2014/023715
§ 371 (c)(1),
(2) Date: Sep. 9, 2015

(87) PCT Pub. No.: WO2014/159447
PCT Pub. Date: Oct. 2, 2014

(65) Prior Publication Data
US 2016/0022406 A1 Jan. 28, 2016

Related U.S. Application Data

(60) Provisional application No. 61/782,002, filed on Mar. 14, 2013.

(51) Int. Cl.
*A61F 2/01* (2006.01)
*A61F 2/24* (2006.01)
(52) U.S. Cl.
CPC ............ *A61F 2/013* (2013.01); *A61F 2/2418* (2013.01); *A61F 2002/011* (2013.01)

(58) Field of Classification Search
CPC ....... A61F 2/2436; A61F 2/2427; A61F 2/013
See application file for complete search history.

(56) References Cited

U.S. PATENT DOCUMENTS 6,152,946 A 11/2000 Broome et al.
6,746,469 B2 6/2004 Mouw
(Continued)

FOREIGN PATENT DOCUMENTS

WO WO-98/50103 A1 11/1998
WO WO-03/002031 A2 1/2003
(Continued)

OTHER PUBLICATIONS

Extended European Search Report dated Nov. 28, 2016, which issued in European Application No. 14772621.0.
(Continued)

*Primary Examiner* — Katherine M Rodjom
(74) *Attorney, Agent, or Firm* — Nathan S. Smith; Sujohn Das; Morgan, Lewis & Bockius LLP

(57) ABSTRACT

Devices and methods for providing protection from embolisms and microembolisms in a subject undergoing catheter-based intravascular procedures. The embolic protection devices have an expandable support frame comprising u-shaped members and leg members which facilitate proper placements in a defective valve annulus. The filtering devices expand in the vessels and allow blood flow to continue through the vessels, thereby catching and removing debris of the flowing blood. Also disclosed are embolic protection devices for use with a sutureless valve prosthesis which is implanted via catheter-based methods.

19 Claims, 10 Drawing Sheets

(56) References Cited

U.S. PATENT DOCUMENTS

| | | | |
|---|---|---|---|
| 8,366,768 | B2 | 2/2013 | Zhang |
| 2002/0161390 | A1 | 10/2002 | Mouw |
| 2003/0004540 | A1 | 1/2003 | Linder et al. |
| 2006/0149313 | A1 | 7/2006 | Arguello et al. |
| 2009/0024157 | A1 | 1/2009 | Anukhin |
| 2009/0054969 | A1* | 2/2009 | Salahieh ............... A61F 2/2418 623/1.26 |
| 2012/0330346 | A1 | 12/2012 | Frimerman |

FOREIGN PATENT DOCUMENTS

| | | |
|---|---|---|
| WO | WO-03/084437 A2 | 10/2003 |
| WO | WO-03/090607 A2 | 11/2003 |
| WO | WO-2006/031648 A2 | 3/2006 |
| WO | WO-2007/047945 A2 | 4/2007 |
| WO | WO-2007/075959 A2 | 7/2007 |
| WO | WO-2010/117680 A1 | 10/2010 |
| WO | WO-2011/068924 A1 | 6/2011 |
| WO | WO 2014/159447 A2 | 10/2014 |

OTHER PUBLICATIONS

International Search Report from PCT Patent Application No. PCT/US2014/023715 dated Sep. 11, 2014, application now published as International Publication No. WO2014/159447 on Oct. 2, 2014.

Chinese Office Action dated Dec. 29, 2016, which issued in Chinese Application No. 201480024531.2.

Partial Supplementary European Search Report dated Aug. 18, 2016, which issued in European Application No. 14772621.0.

* cited by examiner

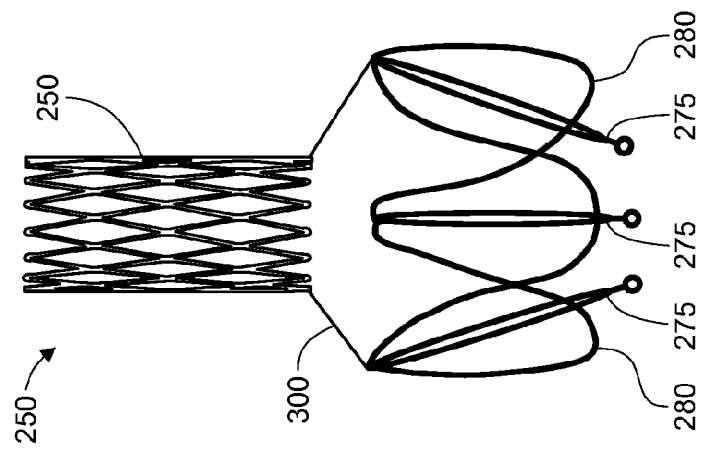
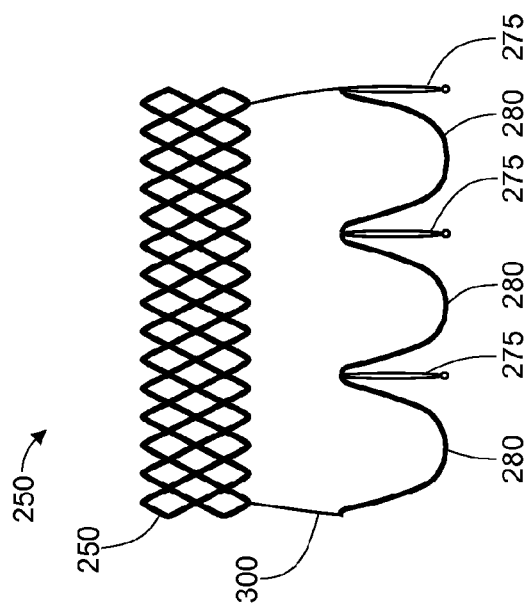

# EMBOLIC PROTECTION DEVICES AND METHODS OF USE

CROSS REFERENCE TO RELATED APPLICATIONS

This application is a U.S. National Stage of International Patent Application No. PCT/US2014/023715, filed Mar. 11, 2014, which claims the benefit of priority to U.S. Provisional Application No. 61/782,002, filed Mar. 14, 2013, the disclosures of which are all incorporated herein by reference in their entirety.

TECHNICAL FIELD

The present disclosure is directed to apparatuses and devices for reducing the incidence of embolisms during and/or after cardiac valve replacement or implantation procedures.

BACKGROUND

Minimally invasive procedures have become increasingly popular for use in cardiac valve delivery, but there remain significant challenges in replacing a diseased cardiac valve without cardiopulmonary bypass. One is preventing cardiac failure during valve treatment while another is treating a valve without causing stroke or other ischemic events that might result the replacement procedure. Such downstream negative effects can be both immediate and delayed. For example, particulate material liberated while manipulating the native and prosthetic valves within the patient may result in embolization into distal vascular beds. Alternatively, such procedures may cause release of soluble mediators which cause the production and/or release of embolic debris. Accordingly, many patients suffering from cardiovascular disease have a higher risk of suffering from embolisms and greater care must be taken to minimize such risk in these patients.

There are four primary methods for providing embolic protection with catheter-based interventions. These include distal occlusion, distal filtering, proximal occlusion, and local plaque trapping. The occlusion methods involve occluding blood flow during target vessel intervention, then evacuating debris particles prior to restoring blood flow. While occlusion methods are simple and convenient, weaknesses of the methods include possible shunting of debris into side branches and the need for several minutes of end-organ ischemia caused by occlusion throughout the intervention. Distal filtering allows ongoing perfusion while trapping some debris, but the larger-diameter sheath generally required to maintain most filters in their collapsed state during advancement across the lesion, with potential dislodgement of debris, and reduced maneuverability of integrated-filter guidewire systems may pose significant problems.

It has not yet been definitively shown whether embolism protection is better achieved by occlusion or filtering methods. However, either would benefit from the development of devices and methods which decrease the inherent risk of embolism which accompanies percutaneous methods. Specifically, the potential damage which occurs upon passage of the devices through the vessels. Accordingly, it is desirable to refine all percutaneous devices to minimize this risk by means such as decreasing sheath diameters, increasing device flexibility and minimizing distance traveled by the device through the vessels. Disclosed herein are devices and methods for filtering embolic protection devices designed to minimize those risks inherent with percutaneous interventions,

BRIEF SUMMARY

The foregoing examples of the related art and limitations related therewith are intended to be illustrative and not exclusive. Other limitations of the related art will become apparent to those of skill in the art upon a reading of the specification and a study of the drawings.

In a first aspect, an embolic protection device is provided comprising a filter frame and a filter sheet.

In one embodiment, the filter frame comprises at least 2 u-shaped members. In another embodiment, the filter frame comprises 2, 3, 4, or 5 u-shaped members.

In one embodiment, the filter frame comprises at least 2 leg members. In another embodiment, the filter frame comprises 2, 3, 4, or 5 leg members. In yet another embodiment each leg member is between 2 u-shaped members.

In one embodiment, each of the at least 2 leg members has a proximal and a distal end, wherein the distal end is fixed to a u-shaped member and the proximal end is free. In another embodiment, the proximal end is attached to another of the proximal end of another of the at least 2 u-shaped members.

In one embodiment, the filter frame is fabricated at a single piece.

In one embodiment, the entire length of the filter frame is attached to the filter sheet.

In one embodiment, the filter frame is comprised of a metal. In another embodiment, the filter frame is comprised of a shape memory metal. In another embodiment, the filter frame can have either a compact configuration or an expanded deployed configuration.

In one embodiment, the filter frame has a conical shape when in the expanded configuration. In another embodiment, the filter frame has a proximal end and a distal end, wherein the diameter of the distal end is larger than the diameter of the proximal end when the filter frame is in the expanded configuration. In yet another embodiment, the filter frame has a conical shape.

In one embodiment, the filter frame has a length ranging from about 5 mm to 50 mm, 15 mm to 25 mm or from about 10 mm to 30 mm.

In one embodiment, the filter sheet is attached to the entire length of the filter frame.

In one embodiment, the filter sheet is comprised of a material selected from the group consisting of polyester monofilament mesh, Nylon monofilament mesh, screen printing mesh, nylon mesh, or metallic wire mesh.

In one embodiment, the filter sheet is comprised of a porous material which allows blood to flow freely through the porous material, yet prevents debris from flowing through the material. In one embodiment, the filter sheet comprises pores having a diameter greater than 50 μm, or 100 μm or 170 μm to 250 μm.

In a second aspect, an antegrade embolic protection delivery device is provided, comprising a first sheath and a second sheath, wherein the first sheath and the second sheath are adjacent to each other along a longitudinal axis and wherein the first sheath is distal to the second sheath, and wherein the first sheath encases at least a distal portion of a filter frame and at least a distal portion of a balloon, and wherein the second sheath encases at least a proximal portion of the filter frame and at least a proximal portion of the balloon.

In one embodiment, the delivery device further comprises a control unit which is proximal to the second sheath along the longitudinal axis.

In one embodiment, the first sheath of the antegrade embolic protection delivery device encases the entire filter frame. In another embodiment, the second sheath of the antegrade embolic delivery protection device encases the entire balloon.

In one embodiment, the first sheath of the antegrade embolic protection delivery device has a diameter ranging from about 1 mm to 30 mm or from about 2 mm to about 20 mm. In another embodiment, the diameter of the antegrade embolic protection delivery device does not have the same diameter along its entire length. In still another embodiment, the first sheath of the antegrade embolic protection delivery device has a conical shape. In yet another embodiment, the first sheath has an opening at both its proximal end and its distal end.

In one embodiment, the second sheath of the antegrade embolic protection delivery device has a diameter ranging from about 1 mm to 30 mm or from about 2 mm to about 20 mm.

In one embodiment the first and/or second sheath of the antegrade embolic protection delivery device is straight. In another embodiment, the first and/or second sheath is curved. In another embodiment, the first and/or second sheath has a flexibility which allows it to conform to a curved path of the vessel through which the first and/or second sheath is advanced.

In a third aspect, a retrograde embolic protection delivery device is provided, comprising a first sheath and a second sheath, wherein the first sheath and the second sheath are adjacent to each other along a longitudinal axis and wherein the first sheath is distal to the second sheath, wherein the first sheath encases at least a distal portion of a vessel filter and at least a distal portion of a balloon, wherein the second sheath encases at least a proximal portion of the vessel filter and at least a proximal portion of the balloon, and wherein the first sheath and the second sheath are adjacent to each other along a longitudinal axis and wherein the first sheath is distal to the second sheath.

In one embodiment, the delivery device further comprises a control unit which is proximal to the second sheath along the longitudinal axis.

In one embodiment, the first sheath (nose cone) of the retrograde embolic delivery protection device has a diameter ranging from about 1 mm to 30 mm or from about 2 mm to about 20 mm. In another embodiment, the diameter of the retrograde embolic protection delivery device does not have the same diameter along its entire length. In still another embodiment, the retrograde embolic protection delivery device has a conical shape. In yet another embodiment, the first sheath has an opening at both its proximal end and its distal end.

In one embodiment, the second sheath of the retrograde embolic protection delivery device has a diameter ranging from about 1 mm to 30 mm or from about 2 mm to about 20 mm. In another embodiment, the diameter of the retrograde embolic protection delivery device does not have the same diameter along its entire length.

In one embodiment the first and/or second sheath of the retrograde embolic protection delivery device is straight. In another embodiment, the first and/or second sheath is curved. In yet another embodiment, the first and/or second sheath has a flexibility which allows it to conform to a curved path of the vessel through which the first and/or second sheath is advanced.

In a fourth aspect, a valve prosthesis with embolic protection device comprising a support frame comprising a plurality of flexible leaflets attached to the support frame to provide a one-way valve in the orifice when the support frame is in its expanded condition, a moveably attached valve clasper, and a filter sheet is provided.

In one embodiment, the support frame is radially expandable between a compact condition and an expanded condition, the support frame having an outer surface and defining a central orifice about an axis along an inflow-outflow direction. In another embodiment, the support frame comprises a plurality of flexible links arranged wherein one portion of the support frame can expand independently of the remaining portion. In still another embodiment, the valve prosthesis is a sutureless cardiac valve prosthesis.

In one embodiment, the moveably attached clasper is reversibly attached to the support frame wherein the clasper is moveable along the longitudinal axis of the support frame relative to the support frame. In another embodiment, the longitudinal movement is between a nesting position with the outer surface of the support frame and an engagement position.

In one embodiment, the at least one valve clasper is physically separated from the support frame.

In one embodiment, the at least one valve clasper is comprised of at least one u-shaped member. In another embodiment, the valve clasper further comprises a straight portion which connects a first and a second u-shaped member. In still another embodiment, the at least one valve clasper comprises a u-shaped member and a first and a second leg member.

In one embodiment, the filter sheet is permanently attached to the at least one valve clasper and is permanently attached to the support frame. In another embodiment, the filter sheet is attached to the distal end of the support frame. In one embodiment, the filter sheet provides means for the movable attachment of the valve clasper to the support frames.

In a fifth aspect, a valve prosthesis with embolic protection delivery device is provided comprising a first sheath, a second sheath, and a valve prosthesis with embolic protection device, wherein the valve prosthesis with embolic protection device comprises a support frame with prosthetic valve leaflets, at least one moveably attached valve clasper and a filter sheet.

In one embodiment, the first sheath encases at least a portion of the support frame and the second sheath encases at least a portion of the valve clasper.

In one embodiment, the first sheath is adjacent to and distal to the second sheath along the longitudinal axis of the delivery apparatus.

In one embodiment, the delivery device further comprises a control unit which is proximal to the second sheath along the longitudinal axis.

In one embodiment, the delivery device further comprises a balloon catheter.

In a sixth aspect, a method for reducing the incidence of embolism or microembolism in a subject is provided, comprising use an antegrade embolic protection delivery device in a subject in need thereof, wherein the antegrade embolic protection delivery device encases an embolic protection device and a balloon catheter.

In one embodiment, the method is performed before or during delivery of a cardiac valve prosthesis.

In one embodiment, the method comprises: introducing the distal end of an antegrade embolic protection delivery device into the vessel or body chamber of the subject;

advancing the antegrade delivery device toward a heart valve annulus in the direction of the natural blood flow until the first sheath is past the valve annulus and the second sheath is approximately within the space surrounded by the valve annulus; pushing the first sheath in a distal direction until to uncover a proximal portion of the embolic protection device wherein the proximal portion of the embolic protection device expands to a deployed configuration; pulling the antegrade device in a proximal direction until the proximal end of each of the the embolic protection device u-shaped members contacts a valve leaflet sinus; pulling the second sheath in a proximal direction to fully uncover the balloon catheter; inflating the balloon catheter to dilate the native vessel or valve; deflating the balloon catheter; pushing the embolic protection device distally while holding the first sheath stationary in order to encase the embolic protection device within the first sheath; and pulling the antegrade delivery device proximally to remove it from the vessel of the subject.

In a seventh aspect, a method for reducing the incidence of embolism or microembolism in a subject is provided, comprising use of a retrograde embolic protection delivery device comprising use in a subject in need thereof, wherein the retrograde embolic protection delivery device encases an embolic protection device and a balloon catheter.

In one embodiment, the method comprises: introducing the retrograde delivery device into the vessel of a subject and advancing the retrograde apparatus toward a heart valve annulus in the direction opposite the natural blood flow until the first sheath of the device is within about 75 mm of the heart valve annulus; advancing the first sheath to uncover a portion of each of the embolic protection device u-shaped members and a portion of the balloon; pulling the second sheath in a proximal direction to uncover the remaining portion of the balloon and to fully uncover the u-shaped members of the embolic protection device wherein the u-shaped members of the embolic protection device expand radially to an expanded configuration; advancing the retrograde delivery in a distal direction until each of the u-shaped members of the embolic protection device contacts a valve leaflet sinus, inflating the balloon catheter within the valve annulus; deflating the balloon catheter within the valve annulus; pulling the first sheath in a proximal direction to encase the distal portion of the balloon catheter; pushing the second sheath in a distal direction to encase the u-shaped members of the embolic protection device; and pulling the retrograde delivery device in a proximal direction to remove the delivery device from the vessel of the subject.

In an eighth aspect, a method for delivering a valve prosthesis with embolic protection device to a subject is provided, comprising use of a valve prosthesis with embolic protection delivery device, wherein the valve prosthesis with embolic protection delivery device comprises a first sheath, a second sheath, wherein the first and second sheaths encase a valve prosthesis with embolic protection device. The valve prosthesis with embolic protection device comprises a support frame comprising a plurality of flexible leaflets attached to the support frame to provide a one-way valve in the orifice when the support frame is in its expanded condition, a moveably attached valve clasper, and a filter sheet is provided.

In one embodiment, the method comprises introducing the distal end of the valve prosthesis with embolic protection delivery device into a vessel or chamber of a subject; advancing the distal end of the delivery device through the vessel toward the heart in the direction of blood flow until the distal end of the second sheath is advanced past a cardiac valve annulus; pulling the second sheath in a proximal direction to uncover the valve clasper wherein each of the valve clasper u-shaped members expands radially to a deployed configuration; pulling the first sheath in a proximal direction until the proximal end of the support frame is aligned with the proximal end of the u-shaped members; pulling the delivery device in a proximal direction until each of the u-shaped members of the valve clasper contacts a valve leaflet sinus; pushing the first sheath in a distal direction to uncover and deploy the support frame; and pulling the delivery device in a proximal direction to remove the device from the vessel of the subject.

In an alternative embodiment, after the second sheath is pulled in a proximal direction to uncover the valve clasper u-shaped members, the delivery device is pulled in a proximal direction until each of the u-shaped members of the valve clasper contacts a valve leaflet sinus and then the first sheath is pulled in a proximal direction until the proximal end of the support frame is aligned with the proximal end of the u-shaped members, prior to pushing the first sheath in a distal direction to uncover and deploy the support frame.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE FIGURES

FIGS. 8A and 8B illustrate a valve prosthesis with embolic protection device.

DETAILED DESCRIPTION

Figure 1:
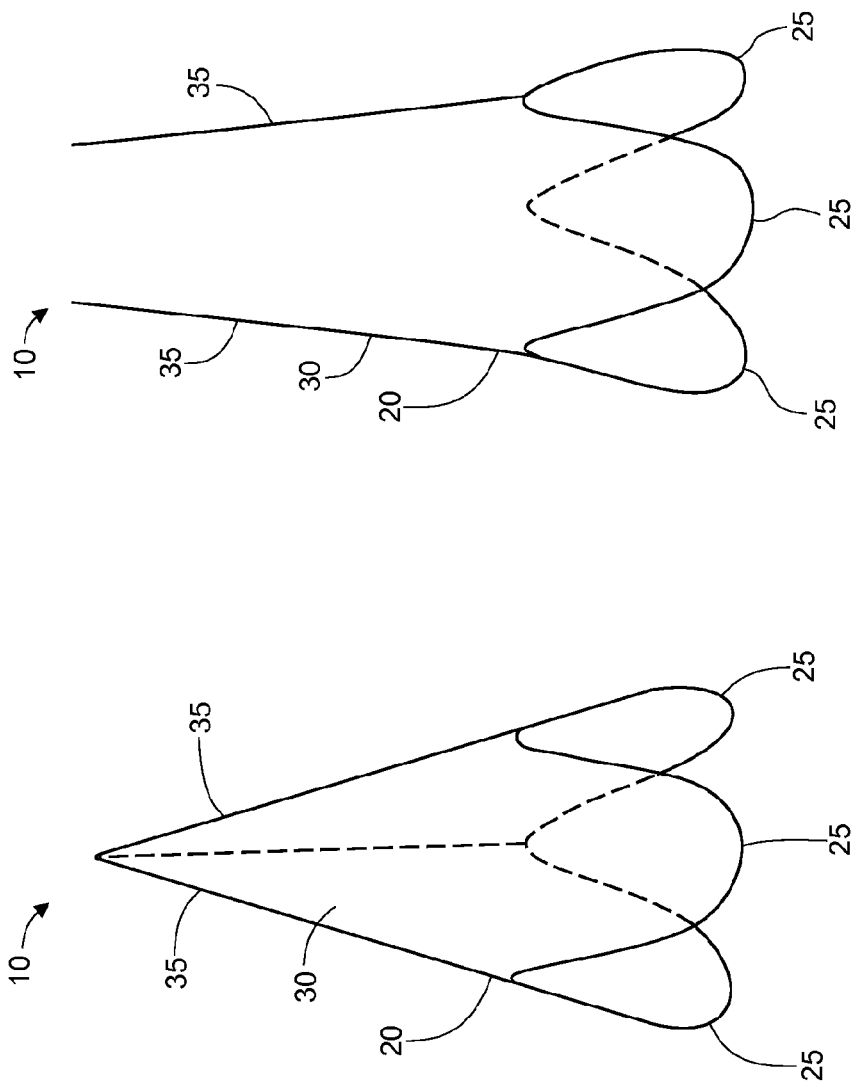
FIGS. 1A and 1B illustrate an embolic protection device.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

As used herein with references to the described devices and apparatuses, the terms "proximal" and "distal" refer to the relative positions of various components of the apparatuses described. Proximal refers to the position closer to the control unit of the apparatus (e.g., the portion of the apparatus held by the practitioner to manipulate separate components of the apparatus during use). Distal refers to the position further from the control unit of the apparatus.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

An "antegrade" delivery device refers to a device which is delivered into the patient, through a vessel (vein or artery) in the direction of the blood flow through that vessel.

A "retrograde" delivery device refers to a device which is delivered into the patient, through a vessel (vein or artery) in the direction opposite that of the blood flow through that vessel.

When describing a delivery device and components thereof, "proximal" refers to a position closest to the operational components held by the user of the device. "Distal" refers to a position closest to the end of the device which first enters the patient and is advanced through the vessel.

II. Embolic Protection Device

Minimally invasive and percutaneous procedures performed for the repair of valves may be preferred over more invasive forms of surgery but still suffer from drawbacks, one of them being disruption of occlusive plaque or thrombus during arterial intervention which can lead to downstream embolization and microvascular obstruction. In the present disclosure, compositions and devices are provided which provide a means for filtering the blood running through blood vessels in a subject to catch and in some cases remove debris such as that resulting form breakage of atherosclerotic plaques or calcium deposits, while not occluding blood flow.

One solution to the problem of emboli or microemboli is to enlarge the internal diameter of the vessel near the valve to be repaired while having a filter temporarily in place near the valve to catch any loose debris created during enlargement of the vessel diameter. Described herein is an embolic protection device 10 which comprises a frame 20 and a filter sheet 30. The frame is comprised of at least 2 leg members and at least 2 u-shaped members. The frame may be comprised of 2, 3 4 or 5 leg members and 2, 3, 4 or 5 u-shaped members, respectively. A preferred embodiment is illustrated in FIGS. 1A and 1B, wherein frame 20 comprises 3 leg members 35 and 3 u-shaped members 25. In some embodiments, frame 20 may be made of a metal, a plastic, or other reversibly expandable material, for example. In other embodiments, frame 20 may be made of a shape memory metal. A filter sheet 30 is attached to the entire length of the filter frame as shown in FIGS. 1A and 1B.

Each of leg members 35 comprise a distal and proximal end, wherein the distal end is fixed to a u-shaped member 25. The proximal end of each of leg members 35 may or may not be attached or fixed to the distal end of the other leg members 35. The vessel filter may be delivered to a subject simultaneously with delivery of a balloon catheter as described in more detail below.

Embolic protection device frame 20 (or embolic protection device 10) is conical in shape when in its expanded or deployed configuration, with a first end having a smaller diameter than a second end. The second end has u-shaped members (25) which are able to seat into corresponding native valve leaflet sinus. Accordingly, when embolic protection device 10 is delivered to the vicinity of the valve annulus, u-shaped members 25 may be manipulated to fit into sinuses of the native valve leaflets. This feature is advantageous for at least two reasons: a practitioner performing the procedure can use tactile means to determine proper location of the vessel filter near the valve annulus and the designed fit of the second end to the valve annulus minimizes the chances of blood and debris contained therein from flowing around the filter thereby allowing the debris to enter the circulatory system, increasing the risk of subsequence embolisms and stroke.

Embolic protection device frame 20 can be self-expanding. In some embodiments, the self-expanding frame can be comprised of a shape-memory metal which can change shape at a designated temperature or temperature range. Alternatively, the self-expanding frames can include those having a spring-bias. The material from which the support frame is fabricated allows the support frame to automatically expand to its functional size and shape when deployed but also allows the support frame to be radially compressed to a smaller profile for delivery through the patient's vasculature. Examples of suitable materials for self-expanding frames include, but are not limited to, medical grade stainless steel, titanium, tantalum, platinum alloys, niobium alloys, cobalt alloys, alginate, or combinations thereof. Examples of shape-memory materials include shape memory plastics, polymers, and thermoplastic materials which are inert in the body. Shape memory alloys having superelastic properties generally made from ratios of nickel and titanium, commonly known as Nitinol, are preferred materials.

Below, an embolic protection device delivery apparatus is described in configurations for both antegrade and retrograde delivery of an embolic protection device and balloon catheter. It is understood that antegrade delivery refers to delivery of the apparatus wherein the apparatus in advanced to the vessel in the same direction of the native blood flow through the vessel. Retrograde delivery refers to the delivery of the apparatus wherein the apparatus is advanced through the vessel in a direction opposite that of the native blood flow through the vessel. As described in more detail below, the embolic protection device is unsheathed and deployed to an expanded condition and seated, via its u-shaped members, in the native valve leaflet sinuses prior to inflation (deployment) of the balloon. After inflation of the balloon enlarges the internal diameter of the vessel or valve annulus, the balloon is deflated, followed by sheathing of the filter and removal of the embolic protection device delivery apparatus.

III. An Antegrade Embolic Protection Delivery Device

Figure 2:
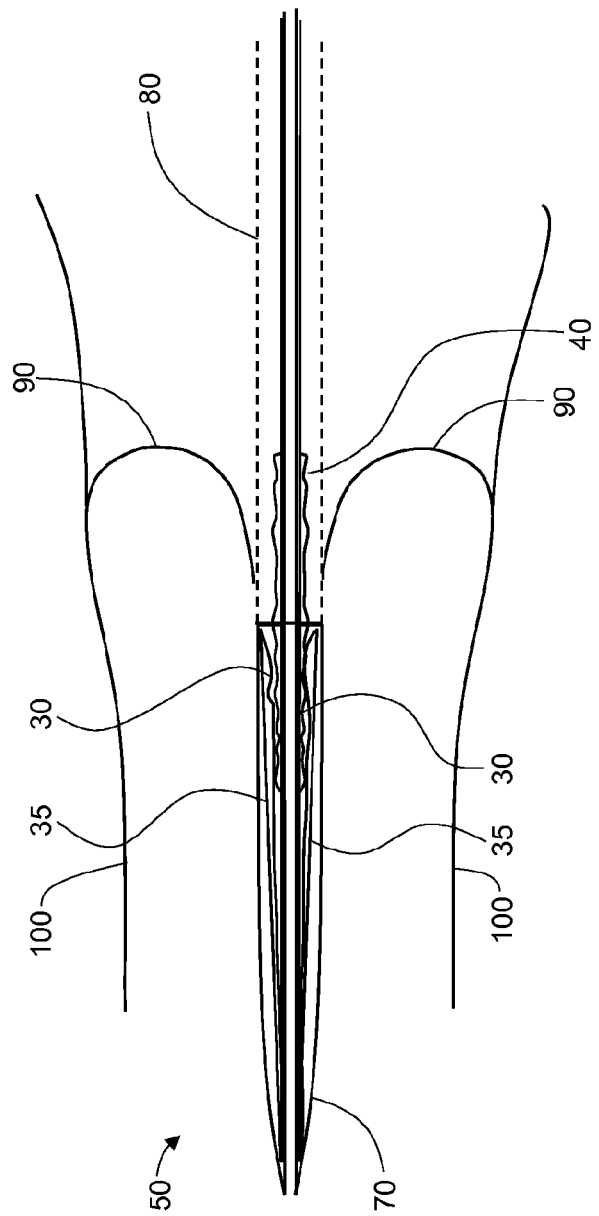
FIG. 2 illustrates an antegrade embolic protection delivery device within a native valve annulus structure.

As shown in FIG. 2, an antegrade embolic protection delivery device 50, comprises a first sheath 70, a second 80 sheath, an embolic protection device, and a balloon catheter 40. To deliver the embolic protection device, the embolic protection device is put into a compact configuration, encased, at least partially, in first sheath 70 and/or second sheath 80.

Figure 3:
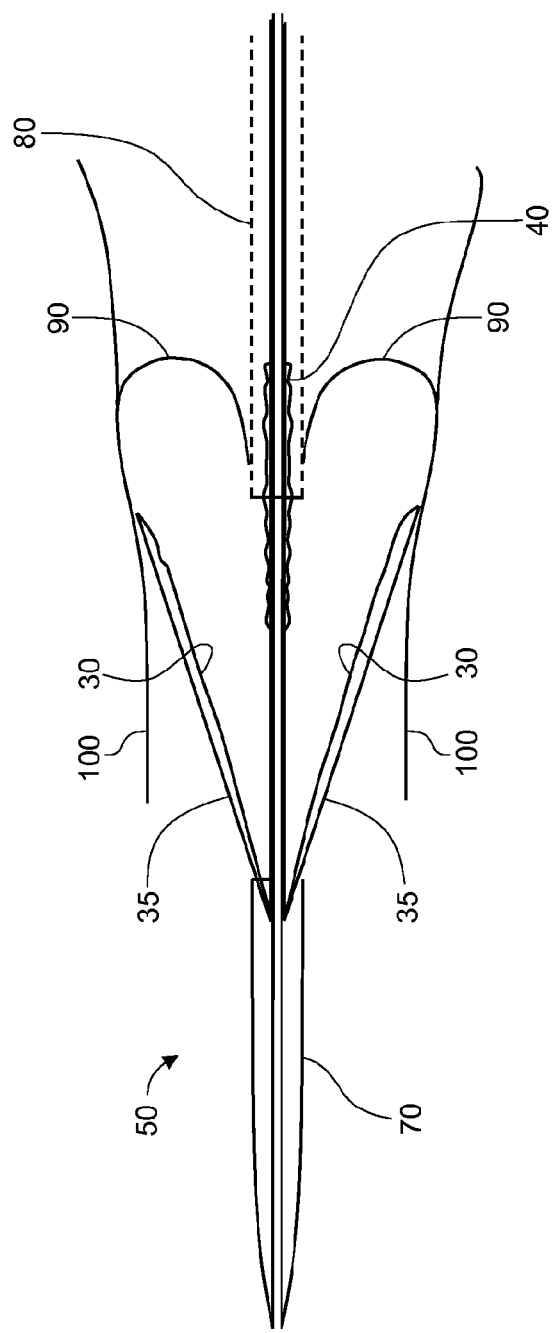
FIG. 3 illustrates an antegrade embolic protection delivery device within a native valve annulus structure.
Figure 4:
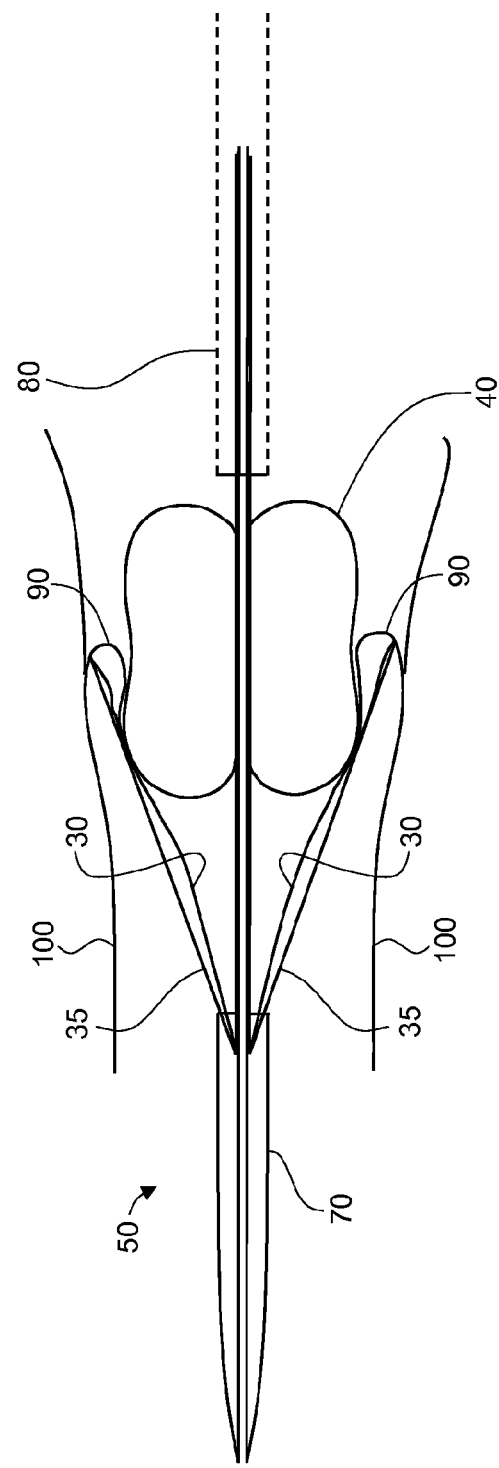
FIG. 4 illustrates an antegrade embolic protection delivery device with inflated balloon catheter within a native valve annulus structure.

A method for using the embolic protection device delivery apparatus to open or expand the inner diameter of a valve in need of repair is illustrated in FIGS. 2-4. Antegrade embolic protection device delivery apparatus 50 is introduced into the vessel of a subject and advanced through the vessel in the direction of native blood flow (in a distal direction). In one embodiment, the apparatus is used to expand the inner diameter of an aortic valve annulus and the antegrade apparatus is delivered via apical delivery, wherein an introducer or trocar is inserted through the chest wall of the subject and into the left ventricle of the subject's heart. However, it is understood that antegrade embolic protection device delivery apparatus 50 can be used for enlarging, prior to repair of, other cardiac valve annuli such as that of the pulmonary valve, the mitral valve or the tricuspid valve.

As shown in FIG. 2, the distal end of antegrade apparatus 50 is advanced past a native valve 90 (e.g., through the left ventricle, past the aortic valve and into the aorta). First sheath 70 is advanced independently to uncover embolic protection device 60, thereby allowing radial expansion of embolic protection device u-shaped members 35 (FIG. 3). Embolic protection device 60 is then moved independently of balloon catheter 40 until u-shaped members 35 of embolic protection device 60 contact the sinuses of the native valve leaflets (FIG. 4). In some embodiments, movement of embolic protection device 60 is not independent of one or more other parts of the device. At this time, second sheath 80 is moved independently in a proximal direction to uncover balloon catheter 40 and balloon catheter 40 is inflated to apply outward pressure on the native valve annulus (FIG. 4). Filter sheet 30 is also shown Balloon catheter 40 is then deflated, second sheath 80 is moved in a distal direction to at least partially encase balloon catheter 40 and first sheath 70 is moved in a proximal direction to at least partially cover embolic protection device 60. At this time, embolic protection device 60 and balloon catheter 40 are encased within the first sheath 70 and second sheath 80 of antegrade valve implantation apparatus 50 to allow safe and easy removal of antegrade valve implantation apparatus 50 from the subject.

IV. A Retrograde Embolic Protection Delivery Device

In another embodiment, a delivery apparatus for retrograde delivery of an embolic protection device with balloon catheter is provided. Retrograde delivery refers to the delivery of the device through the vessel of a subject in a direction opposite that of the natural blood flow within the vessel. For example, such a device may be used with delivering and deploying an aortic valve prosthesis, wherein the protection device and balloon catheter are delivered in a retrograde fashion through the aorta. It is noted that a retrograde valve implantation apparatus comprising an embolic protection device and optionally a balloon catheter can be used in the treatment of other cardiac valves, such as the pulmonary, mitral and tricuspid valves.

Figure 5:
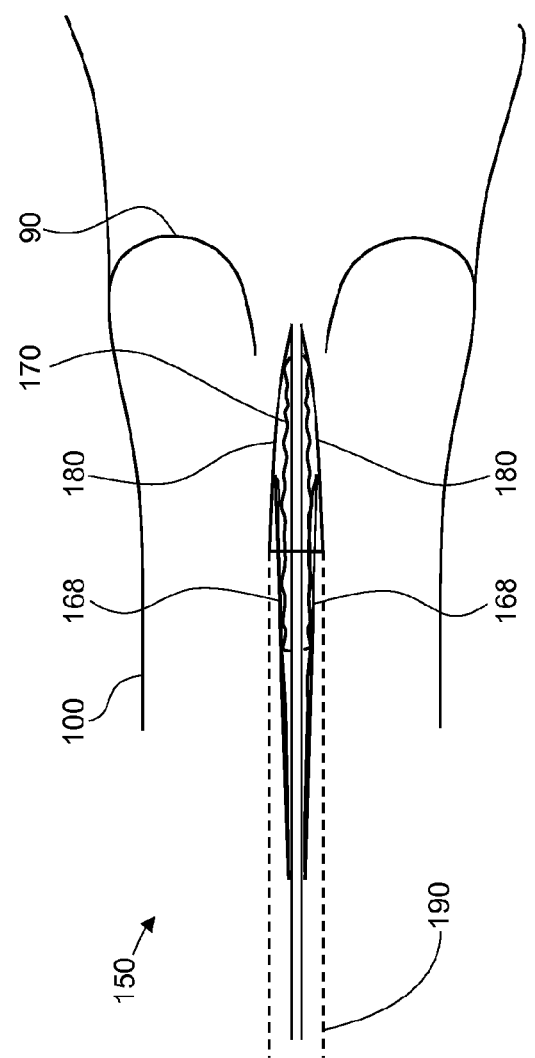
FIG. 5 illustrates a retrograde embolic protection delivery device within a native valve annulus structure.
Figure 6:
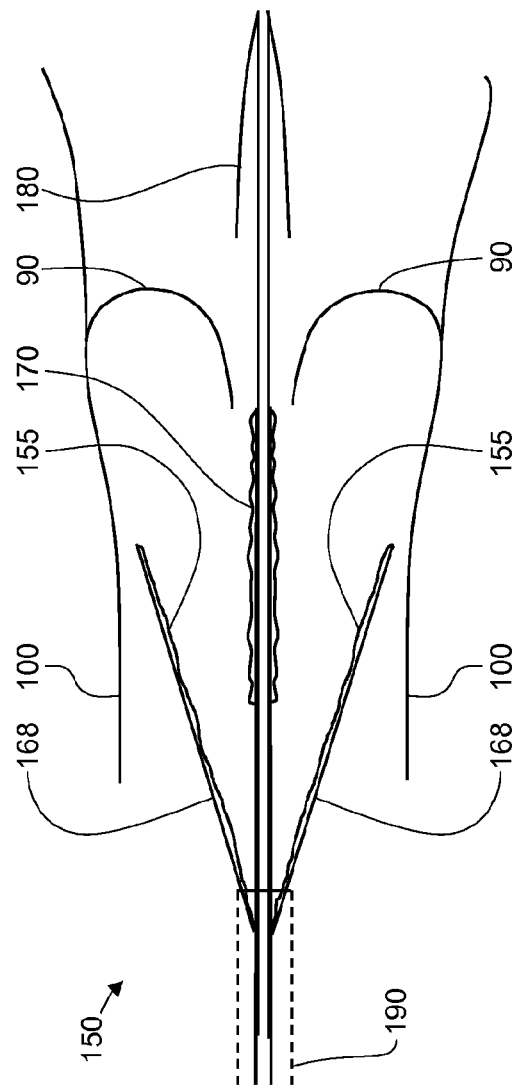
FIG. 6 illustrates a retrograde embolic protection delivery device within a native valve annulus structure.
Figure 7:
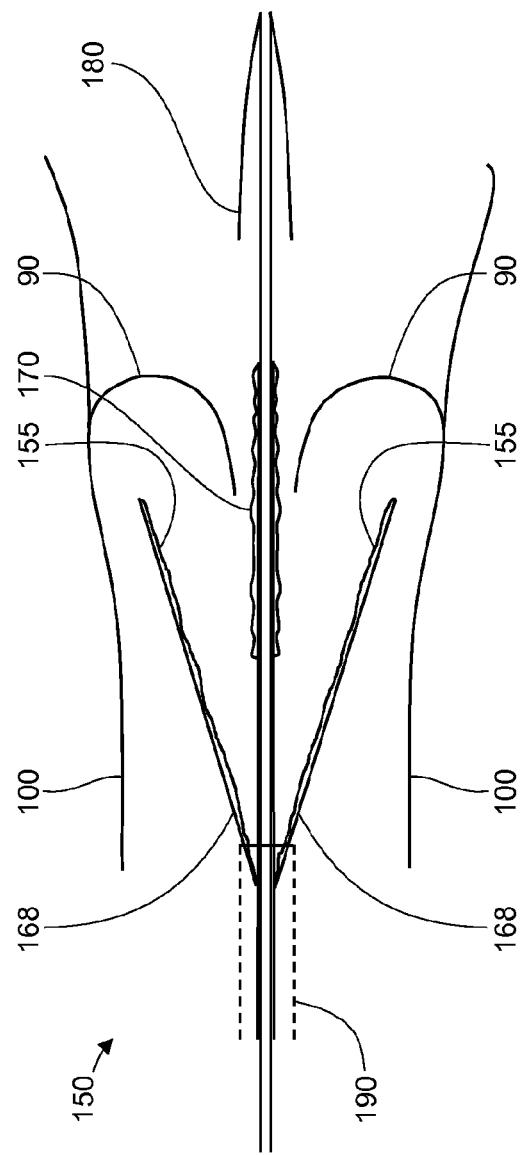
FIG. 7 illustrates a retrograde embolic protection delivery device within a native valve annulus structure.

As shown in FIGS. 5-7, the distal end of a retrograde valve implantation apparatus 150 is advanced past the native valve 90 (e.g., advanced through the aorta, past the aortic valve, into the left ventricle). Second sheath 190 is pulled back independently to uncover embolic protection device 160, thereby allowing radial expansion of u-shaped members 168 of embolic protection device frame 165 (FIG. 6). Filter sheet 155 is also shown. Embolic protection device 160 is then moved independently in a distal direction until each of u-shaped members 168 of embolic protection device 160 contacts the sinus of a native valve leaflet 90 (FIG. 7). At this time, first sheath 180 is advanced independently in a distal direction to uncover balloon catheter 170 (FIG. 8) and balloon catheter 170 is inflated to apply outward pressure on the native valve annulus. Balloon catheter 170 is then deflated, first sheath 180 is moved in a proximal direction to at least partially encase balloon catheter 170, and second sheath 190 is moved in a distal direction to at least partially cover embolic protection device 160. At this time, embolic protection device 160 and balloon catheter 170 are encased within the first and second sheaths of antegrade valve implantation apparatus 150 to allow safe and easy removal of antegrade valve implantation apparatus 150 from the subject.

V. A Valve Prosthesis with Embolic Protection Device

In one aspect, a valve prosthesis is provided wherein the prosthesis comprises a filter (embolic protection material) which may be attached to a support frame and to at least one moveably attached valve clasper. The support frame with at least one moveably attached valve clasper is fully described in U.S. Pat. No. 8,366,768, the contents of which are incorporated herein by reference in their entirety.

Having an embolic protection device associated with the valve prosthesis is advantageous at least in part because the practitioner is able to address the problem of emboli resulting from the process of implanting the valve prosthesis while implanting the valve prosthesis.

A valve prosthesis with embolic protection device is illustrated in FIGS. 8A-8B. FIG. 8A shows an example of an embolic protection device 250 (in a flat view), which is radially expandable between a compact condition and an expanded condition, the support frame having an outer surface and defining a central orifice about an axis along an inflow-outflow direction. Attached to the inner surface of the support frame is a plurality of prosthetic valve leaflets having surfaces defining a reversibly sealable opening for unidirectional flow of a liquid through the prosthetic valve. The prosthetic valve can include three valve leaflets for a tri-leaflet configuration. As appreciated, mono-leaflet, bi-leaflet, and/or multi-leaflet configurations are also possible. For example, the valve leaflets can be coupled to the valve frame so as to span and control fluid flow through the lumen of the prosthetic valve.

In some embodiments, the leaflets comprise synthetic material, engineered biological tissue, biological valvular leaflet tissue, pericardial tissue, cross-linked pericardial tissue, or combinations thereof. In other embodiments, the pericardial tissue is selected from but not limited to the group consisting of bovine, equine, porcine, ovine, human tissue, or combinations thereof. It is understood that in some embodiments, the number of valve claspers will equal of the number of native leaflets within the native valve being treated. The support frame is made of a reversibly expandable material such as a shape memory metal. In one embodiment, the support frame is tubular in shape, has a lattice structure, and has a length L. In another embodiment, the support frame in its expanded condition has a radius r. In some embodiments, the support frame is balloon-expandable.

The support frame may or may not be covered with a covering such as a fabric or other similar material. Any suitable lightweight, durable, flexible, fluid impervious, and/or biocompatible material may be utilized for the covering.

The covering may be attached to the frame utilizing sutures, staples, chemical/heat bonding and/or adhesive. In some embodiments, the covering is a fabric. In further embodiments, the fabric is comprised of, for example, a material identified by a tradename selected from Nylon®, Dacron®, or Teflon®, or is expanded polytetrafluoroethylene (ePTFE), and/or other materials.

The valve prosthesis with embolic protection device comprises a valve clasper movable along the axis between a nesting position with the outer surface of the support frame and an engagement position. A valve clasper 270 is illustrated in FIGS. 8A (flat view) and 8B. Valve clasper 270 is "movably connected" to support frame 260 by a filter sheet 300. Valve clasper 270 is designed to be serially positioned relative to support frame 260 along a longitudinal axis. Accordingly, both valve clasper 270 and support frame 260, when in their compact condition, provide a diameter which readily fits within a sheath or tube structure that can be advanced through vessel walls in the body while causing minimal or no damage to the vessel. Prior to deployment of support frame 260, valve clasper 270 is moved into a position which is concentric to support frame 260. Support frame 260 is can then be deployed such that the native valve leaflet is sandwiched between the external surface of support frame 260 and a u-shaped member 280 of valve clasper 270 to secure the valve prosthesis within the native valve annulus.

Valve claspers are each comprised of a u-shaped member (280 in FIGS. 8A and 8B). In one embodiment, two u-shaped members may be connected via a leg portion (275 in FIGS. 8A and 8B). Thus, a valve clasper having, for example, 3 u-shaped members, will have 3 straight members. Alternatively, a valve clasper may comprise a u-shaped member having a straight leg member on each side of the u-shaped member. Accordingly, a valve clasper having, for example, 3 u-shaped members, will have 6 leg members, wherein there are 2 leg members between 2 u-shaped members.

As illustrated in FIGS. 8A and 8B, a filter sheet 300 is connected to both support frame 260 and valve clasper 270. The filter material has dimensions which allow the at least one valve clasper to be displaced from the support frame along a longitudinal axis, displaced from the support frame along a radial axis, or concentric to the support frame. In one embodiment, the at least one valve clasper is moveably attached to the support frame by the filter material. The filter material any suitable lightweight, durable, flexible, and/or biocompatible material may be utilized for the filter material. The filter may be attached to the frame utilizing sutures, staples, chemical/heat bonding and/or adhesive. The filter is attached in such a way as to prevent passage of debris which is too large to pass through the filter sheet. In some embodiments, the filter is a fabric. In further embodiments, the fabric is comprised of, for example, a material identified by a tradename selected from Nylon®, Dacron®, or Teflon®, or is expanded polytetrafluoroethylene (ePTFE), and/or other materials.

VI. A Valve Prosthesis with Embolic Protection Delivery Device

A valve prosthesis having an embolic protection device as described above can be delivered to a patient in need using a delivery device as described herein. This delivery or implantation device can be designed for antegrade or retrograde delivery of an aortic, pulmonary, mitral or tricuspid valve using minimally invasive procedures as readily understood by a person with ordinary skill in the art.

A valve prosthesis with embolic protection delivery device comprises a first sheath, a second sheath, a valve prosthesis with embolic protection device, and a control unit which allows independent control of at least, for example, the first and second sheaths, the support frame and the valve claspers (as described in U.S. Pat. No. 8,366,768, the contents of which are incorporated herein by reference in their entirety).

Figure 9:
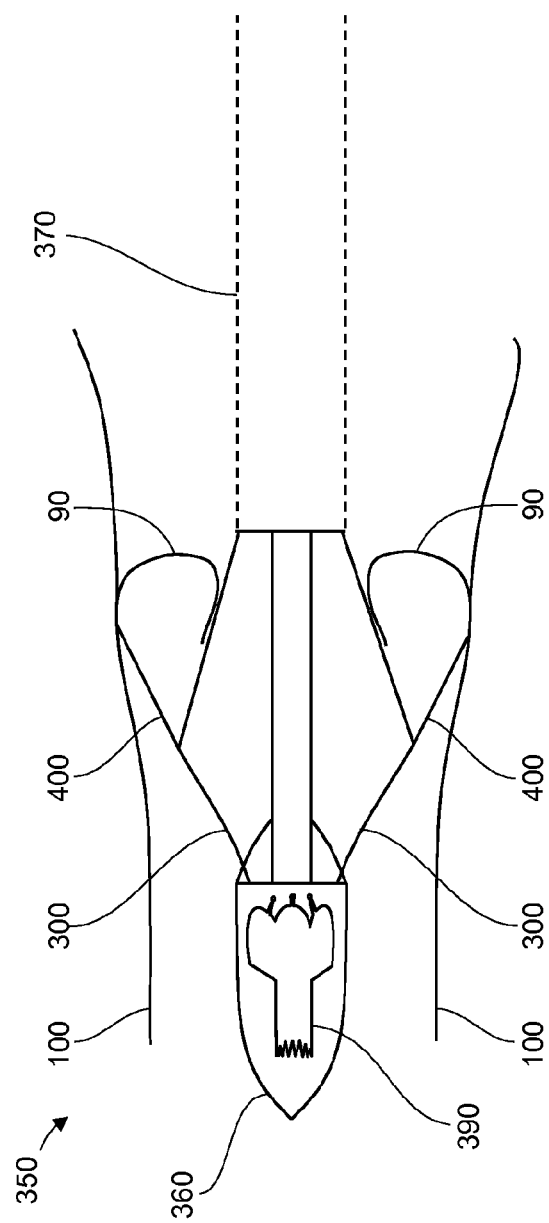
FIG. 9 illustrates a valve prosthesis with embolic protection delivery device.
Figure 10:
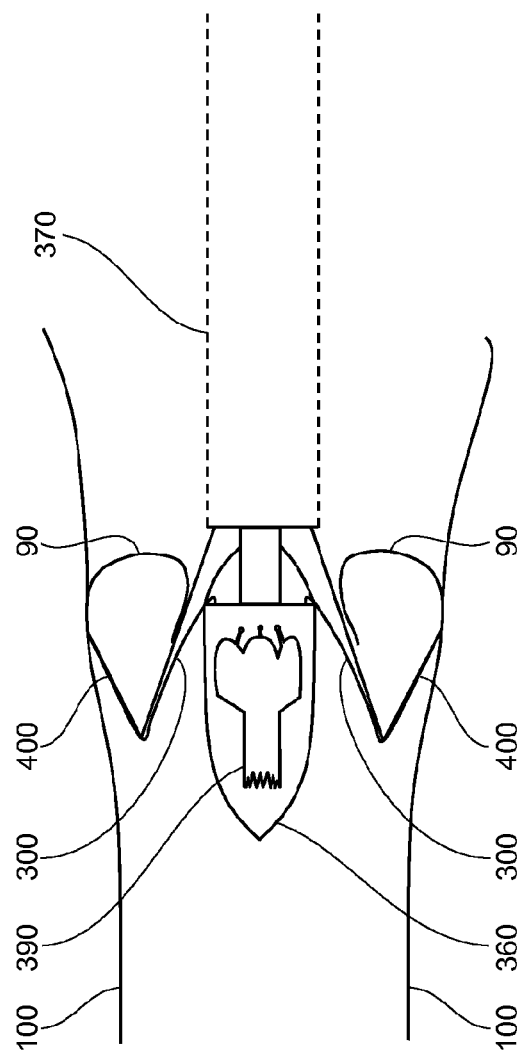
FIG. 10 illustrates a valve prosthesis with embolic protection delivery device.

Use of the delivery device comprising the valve prosthesis with embolic protection is illustrated in FIGS. 9 and 10. In these illustrations, a delivery device is employed in an antegrade delivery process (with the direction of natural blood flow), but it is understood that the device as disclosed herein can be used for retrograde delivery of a valve prosthesis with embolic device.

Prior to delivery of the valve prosthesis, a first sheath 360 encases a support frame 390 of valve prosthesis with embolic protection device, while a second sheath 380, encases valve claspers 380 of the valve prosthesis with embolic protection device. Accordingly, prior to delivery and while the device is being advanced to the valve to be treated, the support frame and valve claspers are in compact configurations, wherein the support frame and valve claspers are adjacent to each other along a longitudinal axis. Importantly, the support frame and valve claspers are moveably connected. As shown in FIGS. 8A and 8B, support frame 260 and valve clasper 270 are moveably connected using a filter sheet 300.

Valve prosthesis with embolic protection delivery device 350 is introduced into the blood vessel or heart chamber of a patient and advanced so that the distal end of first sheath 360 is past the native valve annulus. Second sheath 370 is then pulled independently in a proximal direction to uncover valve clasper 380 to allow u-shaped members 400 of the claspers to deploy radially. Leg members 384 are also shown. First sheath 360 is then moved in a proximal direction to bring first sheath 360 with encased support frame 390 closer to the native valve annulus and in alignment with valve clasper 380. Delivery device is then pulled in a proximal direction until each of u-shaped members 400 contact the commissure (sinus) between each defective valve leaflet 90 and vessel wall 100. In an alternative embodiment, delivery device 350 is pulled in a proximal direction until each of u-shaped members 400 contact the commissure (sinus) between each defective valve leaflet 90 and vessel wall 100, before first sheath 360 is moved in a proximal direction to bring support frame 390 in alignment with valve clasper 380.

Proper alignment of the support frame with the valve clasper is achieved approximately when the proximal edge of the support frame is aligned with the proximal edge of the u-shaped members of the valve clasper.

After support frame 390 is aligned with valve clasper 380, first sheath 360 is moved in a proximal direction to uncover and deploy support frame 390.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An embolic protection delivery device comprising:
   a balloon catheter having an inflatable balloon and first and second ends;

an embolic protection device comprising first and second ends, the first end being coupled relative to the balloon catheter adjacent to the inflatable balloon, the embolic protection device comprising:
- a frame comprising a plurality of leg members coupled to a plurality of U-shaped members, the plurality of leg members extending from the first end of the device toward the second end of the device whereat each of the plurality of leg members is coupled to a respective U-shaped member, the U-shaped members being disposed at the second end of the embolic protection device, the frame defining a frame length from plurality of leg members at the first end to the U-shaped members at the second end; and
- a filter sheet attached to the frame along an entirety of the frame length, wherein the frame and the filter sheet are expandable from a compact state to an expanded state in which the second end is larger than the first end to form a conical shape;
- a first sheath comprising a first inner lumen configured to receive at least a portion of the embolic protection device when the embolic protection device is in the compact state, the first sheath extending distal to the embolic protection device, the first sheath being distally movable relative to the embolic protection device to permit the embolic protection device to expand to the expanded state; and
- a second sheath comprising a second inner lumen configured to receive at least a portion of the embolic protection device when the balloon is in an uninflated state, the second sheath being proximally movable relative to the balloon to permit the balloon to be inflated,
- wherein in the expanded state, the embolic protection device is tactilely manipulable to allow a physician to seat the U-shaped members against native valve leaflet sinuses of a native valve annulus of a patient, the second sheath being thereafter proximally movable to permit the balloon to be inflated against a native valve leaflet for enlarging the valve annulus while the seated embolic protection device minimizes chances of blood and debris contained therein from flowing around the filter thereby allowing the debris to enter a patient's circulatory system.

2. The device according to claim 1, wherein the plurality of U-shaped members comprises three U-shaped members and the plurality of leg members comprises three leg members.

3. The device according to claim 1, wherein each of the leg members has a proximal end which is free.

4. The device according to claim 1, wherein the frame comprises a shape memory metal.

5. The device according to claim 1, wherein the frame in the expanded state comprises a conical shape.

6. The device according to claim 1, wherein the filter sheet comprises a material selected from the group consisting of polyester monofilament mesh, nylon monofilament mesh, screen printing mesh, nylon mesh, or metallic wire mesh.

7. The device according to claim 1, wherein the filter sheet comprises a material which allows blood to flow freely through the filter sheet but collects debris.

8. The device according to claim 1, wherein in the compact state, the embolic protection device axially overlaps the inflatable balloon.

9. The device according to claim 1, wherein upon deflation of the balloon, the first sheath is retractable relative to the embolic protection device to collapse the embolic protection device.

10. The device according to claim 1, wherein in the compact state, the first sheath encases at least a distal portion of the embolic protection device and at least a distal portion of the balloon catheter.

11. The device according to claim 1, wherein in the compact state, the second sheath encases at least a proximal portion of the embolic protection device and at least a proximal portion of the balloon catheter.

12. The device according to claim 1, wherein in the compact state, the first and second sheaths are axially adjacent to each other along a longitudinal axis, wherein the first sheath is distal to the second sheath.

13. The device according to claim 1, wherein the first end of the embolic protection device is positioned distal to the second end of the embolic protection device.

14. The device according to claim 1, wherein the first end of the embolic protection device is coupled relative to the balloon catheter between the catheter first end and the inflatable balloon, distal to the inflatable balloon.

15. The device according to claim 1, wherein the first sheath is proximally movable relative to the embolic protection device when the embolic protection device is in the expanded state to cause the embolic protection device to collapse to the compact state.

16. The device according to claim 1, wherein the first end of the embolic protection device is coupled relative to the balloon catheter proximal to the inflatable balloon.

17. The device according to claim 1, wherein the first sheath is distally movable relative to the balloon to permit the balloon to be inflated.

18. A valve prosthesis with embolic protection, the prosthesis comprising:
- a support frame comprising a plurality of leg members coupled to a plurality of U-shaped members, the plurality of leg members extending from a first end of the prosthesis toward a second end of the prosthesis whereat each of the plurality of leg members is coupled to a respective U-shaped member, the frame defining a frame length from plurality of leg members at the first end to the U-shaped members at the second end, the frame being radially expandable between a compact configuration and an expanded configuration, the support frame having an outer surface and a longitudinal axis and defining a central orifice about an axis along an inflow-outflow direction, wherein the support frame is deployable to secure at least one native valve leaflet between the support frame and at least one of the U-shaped members; and
- a valve clasper movably attached to the support frame via a filter sheet, wherein the filter sheet is attached to the support frame along an entirety of the frame length, the clasper comprises a u-shaped member and two leg members, and wherein the leg members are movable relative to the support frame along the longitudinal axis between a nesting position with the outer surface and an engagement position with the valve annulus.

19. The valve prosthesis according to claim 18, further comprising a prosthetic valve leaflet attached to an inner surface of the support frame.

* * * * *